(12) United States Patent
Echigoya et al.

(10) Patent No.: US 9,738,758 B2
(45) Date of Patent: Aug. 22, 2017

(54) THIOL GROUP-CONTAINING POLYMER, CURABLE COMPOSITION THEREOF AND METHOD OF PRODUCING SAME

(71) Applicant: Toray Fine Chemicals Co., Ltd., Urayasu-shi (JP)

(72) Inventors: Koki Echigoya, Moriyama (JP); Yukiko Hamada, Ichihara (JP); Kazunori Matsumoto, Cangzhou (CN)

(73) Assignee: Toray Fine Chemicals Co., Ltd. (JP)

( * ) Notice: Subject to any disclaimer, the term of this patent is extended or adjusted under 35 U.S.C. 154(b) by 0 days.

(21) Appl. No.: 15/270,263

(22) Filed: Sep. 20, 2016

(65) Prior Publication Data

US 2017/0009019 A1  Jan. 12, 2017

Related U.S. Application Data

(62) Division of application No. 14/416,468, filed as application No. PCT/JP2013/068830 on Jul. 10, 2013.

(30) Foreign Application Priority Data

Aug. 1, 2012 (JP) ................... 2012-170857

(51) Int. Cl.
| | | |
|---|---|---|
| *C08G 75/14* | (2006.01) | |
| *C08G 18/52* | (2006.01) | |
| *C08G 59/56* | (2006.01) | |
| *C08G 59/66* | (2006.01) | |
| *C08G 18/73* | (2006.01) | |
| *C09K 3/10* | (2006.01) | |
| *C08G 59/40* | (2006.01) | |
| *C08L 63/00* | (2006.01) | |
| *C07C 323/14* | (2006.01) | |

(52) U.S. Cl.
CPC ............ *C08G 75/14* (2013.01); *C07C 323/14* (2013.01); *C08G 18/52* (2013.01); *C08G 18/73* (2013.01); *C08G 59/4028* (2013.01); *C08G 59/56* (2013.01); *C08G 59/66* (2013.01); *C08L 63/00* (2013.01); *C09K 3/1012* (2013.01); *C08G 2190/00* (2013.01)

(58) Field of Classification Search
CPC ..................................................... C08G 75/14
See application file for complete search history.

(56) References Cited

U.S. PATENT DOCUMENTS

| | | | |
|---|---|---|---|
| 2,392,402 A | 1/1946 | Patrick | |
| 2,466,963 A | 4/1949 | Patrick et al. | |
| 2,553,206 A | 5/1951 | Patrick | |
| 2,646,415 A * | 7/1953 | Patrick ...................... | C08G 8/10 |
| | | | 525/535 |
| 3,316,324 A | 4/1967 | Mendoyanis | |
| 6,939,941 B2 | 9/2005 | Gilmore et al. | |
| 8,039,561 B2 * | 10/2011 | Saiki ...................... | C07F 7/1836 |
| | | | 525/536 |
| 9,296,890 B2 * | 3/2016 | Suga ...................... | C08G 59/56 |
| 2010/0184899 A1 * | 7/2010 | Rao ........................ | C07C 323/12 |
| | | | 524/392 |
| 2012/0067249 A1 * | 3/2012 | Woods .................. | C07F 7/1836 |
| | | | 106/287.25 |

FOREIGN PATENT DOCUMENTS

| | | |
|---|---|---|
| JP | 62-053354 A | 3/1987 |
| JP | 62-280259 A | 12/1987 |
| JP | 04-363325 A | 12/1992 |
| JP | 05-017684 A | 1/1993 |
| JP | 09-052937 A | 2/1997 |
| JP | 11-060693 A | 3/1999 |
| JP | 2000-345101 A | 12/2000 |
| JP | 2003-128645 A | 5/2003 |
| JP | 2004-149712 A | 5/2004 |
| JP | 2013-127026 A | 6/2013 |
| JP | 2013-129768 A | 7/2013 |
| JP | 2013-144756 A | 7/2013 |
| WO | 98/39365 A2 | 9/1998 |
| WO | 2006/029144 A1 | 3/2006 |
| WO | 2008/040508 A1 | 4/2008 |
| WO | 2009/131796 A1 | 10/2009 |
| WO | 2010/126920 A2 | 11/2010 |
| WO | 2013-018501 A1 | 2/2013 |
| WO | 2013-089000 A1 | 6/2013 |

OTHER PUBLICATIONS

Norman G. Gaylord, "Polyethers, Part III. Polyalkylene Sulfides and Other Polythioethers," Interscience Publishers, vol. 13, 1962, p. 62.
"Polymer Exemption Guidance Manual," US Environmental Protection Agency Office of Pollution Prevention and Toxics, Jun. 1967.
"Guidance for monomers and polymers," Version 2.0, European Chemicals Agency, 2012.
EPO Communication dated Feb. 11, 2015 w/ Third Party Observation dated Jul. 7, 2014 of corresponding European Appln. No. 13825332.3.

(Continued)

Primary Examiner — Megan McCulley
(74) Attorney, Agent, or Firm — DLA Piper LLP (US)

(57) ABSTRACT

A method of producing a thiol group-containing polymer includes reacting bis(2-chloroethyl) formal with sodium hydrosulfide, wherein the thiol group-containing polymer is represented by general formula:

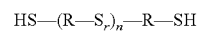

where R is an organic group including a $-C_2H_4-O-CH_2-O-C_2H_4-$ structure, n is an integer of from 1 to 200, r is an integer of from 1 to 5, and the average value of r is 1.1 or more and lower than 1.8, and wherein the thiol group-containing polymer is a liquid polymer.

4 Claims, No Drawings

(56) References Cited

OTHER PUBLICATIONS

Russian Office Action dated Mar. 3, 2016 of corresponding Russian Application No. 2015106941/04, with English translation.
European Communication (Third Party Observation) dated Mar. 22, 2016 of corresponding European Application No. 13825332.3.
European Communication (Third Party Observation) dated Mar. 30, 2016 of corresponding European Application No. 13825332.3.

* cited by examiner

THIOL GROUP-CONTAINING POLYMER, CURABLE COMPOSITION THEREOF AND METHOD OF PRODUCING SAME

TECHNICAL FIELD

This disclosure relates to a thiol group-containing polymer and a method of producing the thiol group-containing polymer. In particular, the disclosure relates to a thiol group-containing polymer useful for polysulfide-based sealants, adhesives and paints having a low specific gravity, a low glass transition temperature, a high heat resistance and improved elastic recovery.

BACKGROUND

Liquid polysulfide polymers have thiol groups at the terminals, and thus are easily oxidized and cured by an oxidizing agent such as lead dioxide and manganese dioxide. Rubber-like cured products obtained by curing polysulfide polymers contain sulfur in the main chain of the molecule, and do not contain double bonds, and thus have excellent features in oil resistance, weather resistance, water tightness and air tightness, and also have fine adhesibility, and thus are widely used as sealants, adhesives and paints.

The most common method of producing a polysulfide polymer is a method of obtaining a liquid polymer through a solid polysulfide described in U.S. Pat. No. 2,466,963. Furthermore, a production method using a phase transfer catalyst has been reported (see U.S. Pat. No. 6,939,941).

The thioether described in WO 2009/131796 is a thioether that does not substantially contain polysulfide bonds, and the reference describes that the thioether is formed into a sealant that is excellent in fuel resistance and the like.

The polythioether polymer described in WO 1998/039365 is a polythioether that does not contain polysulfide bonds and shows excellent low temperature flexibility and fuel oil resistance when it is cured, and thus is used as a sealant as in conventional polysulfide polymers.

A sealant composition that utilizes both of the properties of a polysulfide polymer and a polythioether polymer by blending these polymers is known (see WO 2006/029144).

Conventional polysulfide polymers are excellent in oil resistance, weather resistance, stabilities at low temperatures and high temperatures, and the like, and thus are used in various sealants and adhesives. In addition to those properties, especially in sealants for aircraft, further heat resistance, cold resistance and low specific gravity are required. Furthermore, lowering of viscosity is also desired to decrease solvents in sealants. On the other hand, in construction sealants, excellent weather resistance is required, and elastic recovery for following the motion of a joint is required in the case of application for a sealant on movable part.

SUMMARY

We provide a thiol group-containing polymer having a lower viscosity, a lower specific gravity, a lower glass transition temperature and higher heat resistance than those of conventional polysulfide polymers. Furthermore, we provide a curable composition formed into a sealant, an adhesive or a paint that has a lower specific gravity, a lower glass transition temperature, higher heat resistance, higher elastic recovery and more improved weather resistance than those of curable compositions using conventional polysulfide polymers.

In particular, we provide a thiol group-containing polymer represented by the formula:

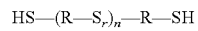
HS—(R—S$_r$)$_n$—R—SH wherein
R is an organic group including a —O—CH$_2$—O— bond and/or a branched alkylene group, n is an integer of from 1 to 200, r is an integer of from 1 to 5, and the average value of r is 1.1 or more and 1.8 or less.

The curable composition is a curable composition comprises the above-mentioned thiol group-containing polymer as a base polymer.

The thiol group-containing polymer has a lower specific gravity, a lower viscosity and a lower glass transition temperature, and higher heat resistance compared to those of conventional polysulfide polymers, by decreasing the repeat number of the sulfur in the polysulfide bonds.

The curable composition has a low specific gravity, a low viscosity and a low glass transition temperature, and the heat resistance, elastic recovery and weather resistance are improved.

The curable composition using the thiol group-containing polymer can be used in sealants, adhesives, paints and the like.

We also provide a method of producing a thiol group-containing polymer comprising reacting bis(2-chloroethyl) formal with sodium hydrosulfide, wherein the thiol group-containing polymer is represented by general formula:

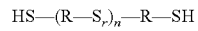
HS—(R—S$_r$)$_n$—R—SH where R is an organic group including a —C$_2$H$_4$—O—CH$_2$—O—C$_2$H$_4$— structure, n is an integer of from 1 to 200, r is an integer of from 1 to 5, and the average value of r is 1.1 or more and lower than 1.8, and wherein the thiol group-containing polymer is a liquid polymer.

We further provide a method of producing a thiol group-containing polymer comprising reacting bis(2-chloroethyl) formal and 1,2,3-trichloropropane with sodium hydrosulfide, wherein the thiol group-containing polymer is represented by general formula:

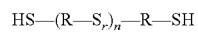
HS—(R—S$_r$)$_n$—R—SH where R is an organic group including a —C$_2$H$_4$—O—CH$_2$—O—C$_2$H$_4$— structure and formula (1):

structure, n is an integer of from 1 to 200, r is an integer of from 1 to 5, and the average value of r is 1.1 or more and lower than 1.8, and wherein the thiol group-containing polymer is a liquid polymer.

DETAILED DESCRIPTION

Our polymers and compositions will be explained below in detail.

We provide a thiol group-containing polymer represented by the formula:

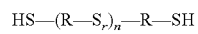
HS—(R—S$_r$)$_n$—R—SH wherein
R is an organic group including a —O—CH$_2$—O— bond and/or a branched alkylene group, n is an integer of from 1 to 200, r is an integer of from 1 to 5, and the average value of r is 1.1 or more and 1.8 or less.

R is preferably an organic group including a —O—CH$_2$—O— bond and a branched alkylene group. The branched alkylene group is preferably from 0 to 70 mol % with respect to the molar number of the —O—CH$_2$—O— bond.

R preferably includes 50 mol % or more of —C$_2$H$_4$—O—CH$_2$—O—C$_2$H$_4$—. More preferably, R includes 70 mol % or more of —C$_2$H$_4$—O—CH$_2$—O—C$_2$H$_4$—.

The branched alkylene group is preferably a multifunctional component derived from a trihaloorganic compound, and is an organic group represented by

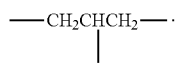

Preferable branched trihaloorganic compounds are trihaloalkyl compounds, and more preferable branched trihaloorganic compounds are trihalopropanes. Preferable halogen atoms for the trihalopropanes are chlorine, bromine and iodine, and a more preferable halogen atom is a chlorine atom.

The r in the thiol group-containing polymer HS—(R—S$_r$)$_n$—R—SH is an integer of from 1 to 5, and is preferably an integer of 1 to 3. The average value of r is 1.1 or more and 1.8 or less. When the average value of r is lower than 1.1, the ultraviolet absorbability due to the polysulfide bonds is lowered and, thus, the weather resistance and hardness after curing become poor. When the average value of r exceeds 1.8, significant effects of a low viscosity, a low specific gravity, a low glass transition temperature, high heat resistance and the like cannot be obtained.

The preferable range of the average value of r differs depending on the use and purpose for which the polysulfide polymer is used.

For example, when a low Tg, a low specific gravity, a low viscosity and heat resistance are required more in use in an aircraft sealant, the average value of r is preferably 1.1 or more and 1.5 or less, and further preferably, when the average value is 1.1 or more and 1.3 or less, the intended effect is high. Even in use in an aircraft sealant, when a low Tg, a low specific gravity and a low viscosity, as well as a high hardness after curing are considered to be important, the average value of r is preferably 1.3 or more and 1.8 or less and, more preferably, when the average value is 1.3 or more and 1.5 or less, the balance among the required performances is good.

In use in a construction sealant, when elastic recovery and heat resistance are required more, the average value of r is preferably 1.1 or more and 1.5 or less, and more preferably, when the average value is 1.1 or more and 1.3 or less, the intended effect is high. Even in use in an architectural sealant, when elastic recovery and heat resistance, as well as weather resistance are considered to be important, the average value of r is preferably 1.3 or more and 1.8 or less and, more preferably, when the average value is 1.3 or more and 1.5 or less, the balance among the required performances is good.

In the thiol group-containing polymer, n is an integer of from 1 to 200, n is preferably an integer of from 1 to 50, more preferably from 5 to 50. The thiol group-containing polymer is a liquid at room temperature, and has a number average molecular weight of preferably from 500 to 50,000, more preferably from 1,000 to 10,000.

To obtain the thiol group-containing polymer, a production method of obtaining a liquid polymer via a solid polysulfide, which is the most common as a conventional method of producing a polysulfide polymer, a method using a phase transfer catalyst, a method by reacting a terminal halogenated sulfur-containing polymer with sodium hydrosulfide and the like are exemplified. A method using a phase transfer catalyst and a method of reacting a terminal halogenated sulfur-containing polymer with sodium hydrosulfide are especially preferable.

Our polymer maintains a structure of a conventional polysulfide polymer, i.e., is a polymer containing —O—CH$_2$—O— bonds, and is different in structure from a blend polymer of polymers having different structures such as a polysulfide polymer and "Permapol P3," which is a polythioether polymer being completely free from —O—CH$_2$—O— bonds, which is described in WO 2006/029144.

The sulfur in the thioether described in WO 2009/131796 correspond to only thioether (—S—) bonds, i.e., the average value of r is 1.0, whereas the polymer has an average value r of the sulfur in HS—(R—S$_r$)$_n$—R—SH of 1.1 or more and 1.8 or less.

The thiol group-containing polymer has a glass transition temperature of preferably −85° C. or more and −50° C. or less and, more preferably, the glass transition temperature is −85° C. or more and −75° C. or less when the viscosity of the polymer is lower than 1 Pa·s, −75° C. or more and −65° C. or less in the case when the viscosity of the polymer is 1 Pa·s or more and lower than 5 Pa·s, −75° C. or more and −55° C. or less when the viscosity of the polymer is 5 Pa·s or more and lower than 45 Pa·s, and −60° C. or more and −50° C. or less when the viscosity of the polymer is 45 Pa·s or more and lower than 100 Pa·s.

The thiol group-containing polymer has a temperature of 50% weight loss at preferably 300° C. or more and 350° C. or less, more preferably 310° C. or more and 340° C. or less.

The thiol group-containing polymer has a specific gravity at 23° C. of preferably from 1.18 to 1.28, more preferably from 1.20 to 1.27.

The curable composition contains a thiol group-containing polymer represented by the formula:

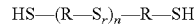

wherein

R is an organic group containing a —O—CH$_2$—O— bond and/or branched alkylene group, n is an integer of from 1 to 200, r is an integer of from 1 to 5, and the average value of r is 1.1 or more and 1.8 or less, and an oxidizing agent.

In the curable composition, as the oxidizing agent, substances that have been used as curing agents for conventional polysulfide polymers can be used. Specific examples of these oxidizing agents include inorganic oxidizing agents, organic peroxides, organic oxidizing agents and the like.

Examples of the inorganic oxidizing agents include inorganic peroxides such as manganese dioxide, lead dioxide, zinc peroxide, calcium peroxide, iron dioxide, barium peroxide, tellurium dioxide, selenium dioxide, tin dioxide, trilead tetraoxide, strontium peroxide and lithium peroxide, inorganic oxides such as zinc oxide, iron(II) oxide, lead oxide, iron(III) oxide, antimony trioxide, magnesium oxide, cobalt oxide, calcium oxide, copper oxide and barium oxide, sodium chromate, potassium chromate, sodium chromate, potassium chromate, sodium perchlorate, sodium perborate, potassium permanganate, sodium percarbonate and the like. Among these, manganese dioxide and dilead oxide are preferable, and manganese dioxide is especially preferable.

The organic peroxides include hydroperoxide, dialkylperoxides, peroxyketals, peroxyesters, peroxydicarbonate, diacylperoxides and the like. Especially, cumenehydroperoxide, p-menthanehydroperoxide, diisopropylbenzenehydroperoxide and t-butylperoxybenzoate are especially excellent in hardness development, and thus are preferable organic peroxides. Two or more kinds of the above-mentioned organic peroxides may be used.

The organic oxidizing agents include nitrobenzene, dinitrobenzene, paraquinonedioxime and the like.

The number of parts to be added of the oxidizing agent is preferably from 1 to 50 parts by weight with respect to 100 parts by weight of the thiol group-containing polymer. When the number is lower than 1 part by weight, a sufficient curing speed cannot be obtained, whereas when the number goes beyond 50 parts by weight, it is not preferable since the polymer is cured immediately after the mixing and thus workability cannot be obtained. The number is more preferably from 1 to 30 parts by weight, even more preferably from 1 to 20 parts by weight, and even more preferably from 5 to 15 parts by weight.

The curable composition contains a thiol group-containing polymer represented by the formula:

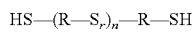

wherein

R is an organic group including a —O—CH$_2$—O— bond and/or a branched alkylene group, n is an integer of from 1 to 200, r is an integer of from 1 to 5, and the average value of r is 1.1 or more and 1.8 or less, and a compound containing two or more isocyanate groups in a molecule.

Examples of the compound containing two or more isocyanate groups in a molecule includes polymethylene polyphenylene polyisocyanate (polymeric MDI), triphenylmethane triisocyanate, dimethyltriphenylmethane tetraisocyanate, biuret forms consist of diisocyanate compounds, trimethylolpropane adducts, isocyanurate trimer and the like.

The diisocyanate compounds include aromatic diisocyanates such as TDI (for example, 2,4-trylenediisocyanate (2,4-TDI), 2,6-trylenediisocyanate (2,6-TDI)), MDI (for example, 4,4'-diphenylmethanediisocyanate (4,4'-MDI), 2,4'-diphenylmethanediisocyanate (2,4'-MDI)), 1,4'-phenylenediisocyanate, xylylenediisocyanate (XDI), tetramethylxylylenediisocyanate (TMXDI), tolidinediisocyanate (TODI) and 1,5-naphthalenediisocyanate (NDI), aliphatic diisocyanates such as ethylenediisocyanate, propylenediisocyanate, tetramethylenediisocyanate, hexamethylenediisocyanate (HDI), trimethylhexamethylenediisocyanate (TMHDI), lysinediisocyanate and norbornanediisocyanate (NBDI), transcyclohexane-1,4-diisocyanate, isophoronediisocyanate (IPDI), or carbodiimide-modified diisocyanates thereof, and the like. Two or more of the above-mentioned isocyanate compounds may be used.

The curable composition contains a thiol group-containing polymer represented by the formula:

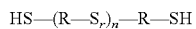

wherein

R is an organic group including a —O—CH$_2$—O— bond and/or a branched alkylene group, n is an integer of from 1 to 200, r is an integer of from 1 to 5, and the average value of r is 1.1 or more and 1.8 or less, an epoxy resin containing two or more glycidyl groups in a molecule, and an amine.

Examples of the epoxy resin containing two or more glycidyl groups in a molecule include epoxy resins each obtained by adding epichlorohydrin to a polyvalent phenol such as bisphenol A, bisphenol F, resorcinol, hydroquinone, pyrocathecol, 4,4-dihydroxybiphenyl or 1,5-hydroxynaphthalene, epoxy resins each obtained by adding epichlorohydrin to a polyvalent alcohol such as ethylene glycol, propylene glycol or glycerin, and epoxy resins each obtained by adding epichlorohydrin to an aromatic dicarboxylic acid such as oxybenzoic acid or phthalic acid, polysulfide polymers having epoxy groups at the terminals (trade names "FLEP-50" and "FLEP-60," both are manufactured by Toray Fine Chemicals Co., Ltd.) and the like, and those being liquids at room temperature are preferable.

It is preferable that the epoxy resin is incorporated so that the incorporation amount thereof becomes from 100 to 1,000 parts by weight with respect to 100 parts by weight of the thiol group-containing polymer. When the above-mentioned incorporation amount is lower than 100 parts by weight, it is not preferable since the hardness and breaking stress become insufficient. More preferably, the incorporation amount is from 100 to 700 parts by weight. Even more preferably, the incorporation amount is from 100 to 600 parts by weight.

The amine may be an amine known as a curing agent for a general epoxy resin. Examples of the amine include aliphatic tertiary amines such as ethylenediamine-diethylenetriamine, triethylenetetramine, pentaethylenehexamine, trimethylenediamine, hex am ethylenediamine and tetramethylenediamine, aliphatic tertiary amines such as N,N-dimethylpropylamine and N,N,N',N'-tetramethylhexamethylenediamine, alicyclic tertiary amines such as N-methylpiperidine and N,N'-dimethylpiperadine, aromatic tertiary amines such as benzyldimethylamine, dimethylaminomethylphenol and 2,4,6-tris(dimethylaminomethyl)phenol, polyamine-epoxy resin adducts obtained by reacting an epoxy resin with an excess amine, polyamine-ethylene oxide adducts, polyamine-propylene oxide adducts, cyanoethylated polyamines, diamines having a silicone as a main chain, or dehydrated condensates obtained by reacting a polyamine with a phenol and an aldehyde, and the like, imidazoles such as 2-ethyl-4-methylimidazole, modified polyamines, and the like.

It is preferable that the amine is incorporated so that the incorporation amount thereof becomes from 1 to 100 parts by weight with respect to 100 parts by weight of the epoxy resin. When the incorporation amount of the amine is from 1 to 100 parts by weight with respect to 100 parts by weight of the epoxy resin, it is advantageous in view of costs since curing is rapid. The incorporation amount is more preferably from 1 to 80 parts by weight, even more preferably from 1 to 60 parts by weight with respect to 100 parts by weight of the epoxy resin.

Where necessary, the curable composition may contain a plasticizer, a filler, a curing promoter, a multifunctional crosslinking agent, an adhesion promoter, an ultraviolet absorber, an antioxidant, a tackifier, a flowable additive, a rubber elastomer, a fungicide, a corrosion inhibitor, a pigment and a masking agent, for the purpose of improving economic efficiency, workability in forming the composition, and the physical properties after curing.

Examples of the plasticizer include phthalic acid esters such as dibutyl phthalate, butyl benzyl phthalate and alkyl (C$_7$-C$_9$)benzyl phthalate, chlorinated paraffin, dipropylene glycol dibenzoate, diethylene glycol dibenzoate, triethylene glycol dibenzoate, dipropylene glycol monobenzoate, hydrogenated terphenyl, hydrocarbon-based plasticizers, halogen terminal sulfur-containing polymers and the like.

The number of parts of the plasticizer to be added is determined depending on the design of the strength and elongation of the cured product, and the viscosity before curing, and is preferably 1 to 100 parts by weight with respect to 100 parts by weight of the thiol group-containing polymer. The number is more preferably from 1 to 50 parts by weight, even more preferably from 1 to 30 parts by weight.

Examples of the filler include inorganic fillers such as calcium carbonate, aluminum oxide, aluminum hydroxide, silica, silicates and sulfate salts, carbon black, and the like. Furthermore, light weight polymer fillers such as polyamides and polyethylenes, silica, hollow fillers such as thermoplastic balloons (thermal expandable microcapsules) of acrylonitrile, metacrylonitrile and vinylidene chloride and the like, thermosetting balloons of phenol, epoxy and the like, and inorganic-based balloons of shirasu, fly ash, glass, alumina and the like, and the like. Two or more kinds of the fillers may be used, and either of the filler whose surface has been treated with an aliphatic acid, a resin acid, a surfactant, a silane coupling agent, paraffin or the like may be used.

The calcium carbonate is preferably heavy calcium carbonate or colloidal calcium carbonate. In general, heavy calcium carbonate is calcium carbonate obtained by mechanically pulverizing and classifying raw stones of limestone to a desired particle size. Colloidal calcium carbonate is calcium carbonate obtained by subjecting raw stones of limestone to mixed combustion with coke or the like to once prepare calcium oxide (quicklime), reacting the calcium oxide with water to give calcium hydroxide (lime hydrate), reacting the calcium hydroxide with carbon gas generated during calcination, and adjusting the particle size and particle shape to desired ones.

The number of parts of the filler to be added is preferably from 0.1 to 500 parts by weight with respect to 100 parts by weight of the thiol group-containing polymer. The number is more preferably from 1 to 300 parts by weight, even more preferably from 10 to 200 parts by weight, even more preferably from 30 to 60 parts by weight.

Examples of the curing accelerator include vulcanization accelerators such as aldehyde-ammonia and aldehyde-amine-based, thiourea-based, guanidine-based, thiazole-based, sulfenamide-based, thiuram-based, dithiocarbamate-based and xanthogenate-based vulcanization accerelators. Specific examples include tris(dimethylaminomethyl)phenol, diphenylguanidine, tetramethylthiuramdisulfide, tetraethylthiuramdisulfide, tetrabutylthiuramdisulfide, hexamethylenetetramine and the like. Two or more kinds of the above-mentioned vulcanization accelerators may be used.

The number of parts of the curing accelerator to be added is determined depending on the curing speed of the curable composition and the working temperature, and is preferably 1 to 10 parts by weight with respect to 100 parts by weight of the thiol group-containing polymer. When the number goes beyond 10 parts by weight, the residual promoter that has not been involved in the reaction may deteriorate the performance of the cured product. The number is more preferably from 1 to 5 parts by weight, even more preferably from 1 to 3 parts by weight.

Examples of the multifunctional crosslinking agent include trimethylolpropane trimercaptopropionate, trimethylolpropane trimercaptoacetate and pentaerythritol-tetrakis-3-mercaptopropionate. Two or more kinds of the above-mentioned multifunctional crosslinking agents may be used.

Examples of the adhesion promoter may include silane coupling agents containing a hydrolyzable silyl group and a reactive organic functional group. Specific examples include vinyl trimethoxysilane, vinyltriethoxysilane, 2-(3,4 epoxycyclohexyl)ethyltrimethoxysilane, 3-glycidoxypropyltrimethoxysilane, 3-glycidoxypropylmethyldiethoxysilane, 3-glycidoxypropyltriethoxysilane, p-styryltrimethoxysilane, 3-methacryloxypropylmethyldimethoxysilane, 3-methacryloxypropyltrimethoxysilane, 3-methacryloxypropylmethyldiethoxysilane, 3-methacryloxypropyltriethoxysilane, 3-acryloxypropyltrimethoxysilane, N-2(aminoethyl)3-aminopropylmethyldimethoxysilane, N-2(aminoethyl)3-aminopropyltrimethoxysilane, N-2(aminoethyl)3-aminopropyltriethoxysilane, 3-aminopropyltrimethoxysilane, 3-aminopropyltriethoxysilane, 3-triethoxysilyl-N-(1,3-dimethyl-butylidene)propylamine, N-phenyl-3-aminopropyltrimethoxysilane, 3-mercaptopropylmethyldimethoxysilane, 3-mercaptopropyltrimethoxysilane, bis(triethoxysilylpropyl)tetrasulfide and the like. Furthermore, a terminal trimethoxysilane-modified polysulfide polymer synthesized by reacting a polysulfide polymer "Thiokol LP-3" and 3-glydoxypropyltrimethoxysilane can also be used as a silane coupling agent. Two or more kinds of these silane coupling agents may also be used.

Examples of the ultraviolet absorbers include benzophenone-based, benzotriazole-based, phenyl salicylate-based, triazine-based, nickel salt and nickel complex salt-based ultraviolet absorber. Specific examples include 2-(2-hydroxy-5-methylphenyl)benzotriazole, 2-[2-hydroxy-3(3,4,5, 6-tetra-hydrophthalic imidomethyl)-5-methylphenyl]benzotriazole, 2-(2-hydroxy-3-t-butyl-5-methylphenyl)-5-chlorobenzotriazole, 2-(2-hydroxy-4-octylphenyl) benzotriazole, 2-(2-hydroxy-3,5-t-butylphenyl) benzotriazole, 2-(2-hydroxy-3,5-t-butylphenyl)-5-chlorobenzotriazole, 2-(2-hydroxy-5-t-octylphenyl) benzotriazole, 2-(2-hydroxy-3,5-di-t-amylphenyl) benzotriazole, nickeldibutyldithiocarbamate, [2,2'-thiobis(4-t-octylphenolate)]-2-ethylhexylamine-nickel and the like.

Examples of the antioxidant include amine-based antioxidants, phenol-based antioxidants, phosphite-based antioxidants and thioether-based antioxidants. Specific examples include 1,3,5-tris[[3,5-bis(1,1-dimethylethyl)-4-hydroxyphenyl]methyl]-1,3,5-triazine-2,4,6(1H,3H,5H)-trione, 1,1, 3-tris(5-tert-butyl-4-hydroxy-2-methylphenyl)butane, 1,1-bis(4-hydroxy-2-methyl-5-tert-butylphenyl)butane, 2,2-bis [[[3-(3,5-di-tert-butyl-4-hydroxyphenyl)propionyl]oxy] methyl]propane-1,3-diol, 1,3-bis[3-(3,5-di-tert-butyl-4-hydroxyphenyl)propionate], bis(3-tert-butyl-4-hydroxy-5-methylbenzenepropaneacid)ethylenebis(oxyethylene), 4,4', 4"-[(2,4,6-trimethylbenzene-1,3,5-triyl)tris(methylene)]tris (2,6-di-tert-butylphenol), and the like.

Examples of the tackifier include phenol resins, coumarone-indene resins, coumarone resins, naphthene-based oils, rosin, rosin esters, hydrogenated rosin derivatives, terpene resins, modified terpene resins, terpene-phenol-based resins, hydrogenated terpene resins, α-pinene resins, alkylphenol-acetylene-based resins, alkylphenol-formaldehyde-based resins, styrene resins, $C_6$-based petroleum resins, $C_9$-based petroleum resins, alicyclic petroleum resins, $C_6/C_9$ copolymerization-based petroleum resins, xylene-formaldehyde-based resins and the like.

Examples of the rubbers and elastomers include natural rubbers, polybutadiene rubbers, acrylic rubbers, polyisoprene rubbers, styrene-butadiene rubbers, acrylonitrile-butadiene rubbers, chloroprene rubbers, olefin-based elastomers, styrene-based elastomers, vinyl chloride-based elastomers, polyester-based elastomers, polyamide-based elastomers, polyurethane-based elastomers, polysiloxane-based elastomers and the like.

EXAMPLES

Our polymers and compositions will further be explained in detail with the following Examples.

Measurement of SH Content

The sample was dissolved in a mixed solution of toluene and pyridine, an aqueous potassium iodide solution was added thereto, and the solution was titrated by using an iodine standard solution.

Measurement of Viscosity

The viscosity of the sample at 25° C. was measured by using a viscometer U-EII manufactured by Toki Sangyo Co., Ltd.

Measurement of Specific Gravity of Polymer

The masses of distilled water and the polymer that had been cured at 23° C. for 24 hours or more were measured by using a container for the measurement of specific gravities under an atmosphere at 23° C. On the presumption that the specific gravity of water is 1.0, the specific gravity of the polymer was calculated from the mass of the polymer with respect to the volume.

Measurement of Specific Gravity of Cured Product

The masses in air and in water were measured under an atmosphere at 23° C., and the specific gravity was calculated by the formula:

Specific gravity=mass in air/(mass in air−mass in water).

Measurement of Glass Transition Temperature ($T_g$)

About 10 mg of the sample was subjected to constant speed temperature rising from −90° C. to 10° C. under nitrogen atmosphere at 10° C./min by using a differential scanning calorimeter DSCQ10 manufactured by TA Instruments. The $T_g$ was obtained from the stepwise signals in the obtained DSC curve.

Measurement of Temperature of 50% Weight Loss

About 30 mg of the sample was subjected to constant-speed temperature rising from room temperature to 500° C. under nitrogen atmosphere at 10° C./min by using a weight measurement apparatus TGAQ50 manufactured by TA Instruments. The temperature at which the weight became 50% of the initial weight in the obtained TGA curve was considered as the temperature of 50% weight loss.

Measurement of Average Value of Sulfur

In the following thiol group-containing polymer:

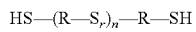

(wherein R is —$C_2H_4$—O—$CH_2$—O—$C_2H_4$—, and n is an integer of from 1 to 200), when r is 2, i.e., when the polymer has disulfide bonds, a strong peak is present in the vicinity of 38.6 to 38.8 ppm when a $^{13}$C-NMR analysis is conducted. When r is 1, i.e., when the polymer has monosulfide bonds, a strong peak is present in the vicinity of 31.6 to 32.2 ppm. In this example, a $^{13}$C-NMR analysis was conducted, the amount of the monosulfide bonds and the amount of the disulfide bonds were respectively obtained from the peak intensities around 32.2 ppm and around 38.8 ppm, and the average sulfur content was quantified. In the $^{13}$C-NMR analysis, a 400 MHz NMR apparatus manufactured by JEOL Ltd. was used, and $CDCl_3$ was used as a solvent.

Evaluation of Accelerated Weather Resistance

The sample was exposed by a Sunshine Weather Meter (S. W. O. M.) in accordance with JIS A 1415 WS-A, and the states of the surface at after 500 hours, 1,000 hours, 1,500 hours and 2,000 hours were observed. The evaluation criteria were as follows, and ○ was judged to be fine.

○: No cracking was observed.
x: Cracking was observed.

Measurement of Elastic Recovery

A curable composition obtained by superposing six sheets each having a thickness of 2 mm was fixed under a 30% compressed state and cured at 90° C. for 24 hours, the composition was then freed from the compression and cured at 23° C. for 24 hours, and the thickness of the product was measured, and the elastic recovery with respect to the heat compression was obtained by the formula:

Elastic recovery (%)=(thickness at restoration−thickness at compression)/(initial thickness−thickness at compression)×100.

Measurement of Dumbbell Tensile Physical Property

Three dumbbell test pieces were cut out from a sheet-like cured product having a diameter of about 120 mm×a thickness of 2 mm by using a punching blade adjusted to the form of dumbbell form No. 5 described in JIS K6251. A gauge line of 20 mm was drawn on each cut dumbbell test piece, and a tensile test was conducted at 500 mm/min by using Tensilon RTA-500 manufactured by Orientec Co., Ltd. In the dumbbell tensile measurement, $M_{100}$ (N/mm$^2$) is the stress at 100% elongation (at the timepoint when the gauge line has become 40 mm), $T_{max}$ (N/mm$^2$) is the maximum tensile stress, and $E_{max}$ (%) is the elongation at the maximum loading. The number of tests was n=3 per one specimen material, and the average value was considered as a measurement result.

Measurement of Hardness

Three dumbbell test pieces were cut out from a sheet-like cured product having a diameter of about 110 mm×a thickness of 2 mm, and four residual sheets were superposed and prepared into a block-like cured product about 50 mm×about 50 mm×8 mm thickness. The cured product formed into a block-like form having a thickness of 8 mm was subjected to a hardness measurement under an atmosphere of 23° C. by a type A durometer described in JIS K6253.

Example 1

Using a 2-L separable flask, 629.2 g of bis(2-chloroethyl) formal, 10.8 g of 1,2,3-trichloropropane, 12.2 g of a 50 wt % aqueous solution of tetrabutylammonium bromide, 572.6 g of a 42% aqueous solution of sodium hydrosulfide, 644 g of water, 78.3 g of sulfur and 254.6 g of a 48% aqueous solution of sodium hydroxide were reacted, whereby a pale yellow clear liquid polymer was obtained without going through a solid polysulfide. The average value of repeating numbers r of sulfur, SH content, viscosity, specific gravity, glass transition temperature and temperature of 50% weight loss of the obtained polymer are shown in Table 1.

Example 2

Using a 2-L separable flask, 629.2 g of bis(2-chloroethyl) formal, 10.8 g of 1,2,3-trichloropropane, 12.2 g of a 50 wt % aqueous solution of tetrabutylammonium bromide, 568.9 g of a 42% aqueous solution of sodium hydrosulfide, 650 g of water, 49.4 g of sulfur and 257.2 g of a 48% aqueous solution of sodium hydroxide were reacted, whereby a pale yellow clear liquid polymer was obtained without going through a solid polysulfide. The average value of repeating numbers r of sulfur, SH content, viscosity, specific gravity, glass transition temperature and temperature of 50% weight loss of the obtained polymer are shown in Table 1.

Example 3

Using a 2-L separable flask, 629.2 g of bis(2-chloroethyl) formal, 10.8 g of 1,2,3-trichloropropane, 12.2 g of a 50 wt % aqueous solution of tetrabutylammonium bromide, 563.7 g of a 42% aqueous solution of sodium hydrosulfide, 659 g of water, 10.0 g of sulfur and 260.5 g of a 48% aqueous solution of sodium hydroxide were reacted, whereby a pale yellow clear liquid polymer was obtained without going through a solid polysulfide. The average value of repeating numbers r of sulfur, SH content, viscosity, specific gravity, glass transition temperature and temperature of 50% weight loss of the obtained polymer are shown in Table 1.

Comparative Example 2

Using a 2-L separable flask, 629.2 g of bis(2-chloroethyl) formal, 10.8 g of 1,2,3-trichloropropane, 12.2 g of a 50 wt % aqueous solution of tetrabutylammonium bromide, 562.4 g of a 42% aqueous solution of sodium hydrosulfide, 661 g of water and 261.4 g of a 48% aqueous solution of sodium hydroxide were reacted, whereby a pale yellow clear liquid polymer was obtained without going through a solid polysulfide. The average value of repeating numbers r of sulfur, SH content, viscosity, specific gravity, glass transition temperature and temperature of 50% weight loss of the obtained polymer are shown in Table 1.

Example 4

Using a 2-L separable flask, 629.2 g of bis(2-chloroethyl) formal, 10.8 g of 1,2,3-trichloropropane, 12.2 g of a 50 wt % aqueous solution of tetrabutylammonium bromide, 528.6 g of a 42% aqueous solution of sodium hydrosulfide, 718 g of water, 87.4 g of sulfur and 284.0 g of a 48% aqueous solution of sodium hydroxide were reacted, whereby a pale yellow clear liquid polymer was obtained without going through a solid polysulfide. The average value of repeating numbers r of sulfur, SH content, viscosity, specific gravity, glass transition temperature and temperature of 50% weight loss of the obtained polymer are shown in Table 1.

Example 5

Using a 2-L separable flask, 629.2 g of bis(2-chloroethyl) formal, 10.8 g of 1,2,3-trichloropropane, 12.2 g of a 50 wt % aqueous solution of tetrabutylammonium bromide, 526.8 g of a 42% aqueous solution of sodium hydrosulfide, 721 g of water, 54.9 g of sulfur and 285.1 g of a 48% aqueous solution of sodium hydroxide were reacted, whereby a pale yellow clear liquid polymer was obtained without going through a solid polysulfide. The average value of repeating numbers r of sulfur, SH content, viscosity, specific gravity, glass transition temperature and temperature of 50% weight loss of the obtained polymer are shown in Table 1.

Example 6

Using a 2-L separable flask, 629.2 g of bis(2-chloroethyl) formal, 10.8 g of 1,2,3-trichloropropane, 12.2 g of a 50 wt % aqueous solution of tetrabutylammonium bromide, 525.7 g of a 42% aqueous solution of sodium hydrosulfide, 723 g of water, 33.0 g of sulfur and 285.9 g of a 48% aqueous solution of sodium hydroxide were reacted, whereby a pale yellow clear liquid polymer was obtained without going through a solid polysulfide. The average value of repeating numbers r of sulfur, SH content, viscosity, specific gravity, glass transition temperature and temperature of 50% weight loss of the obtained polymer are shown in Table 1.

Example 7

Using a 2-L separable flask, 629.2 g of bis(2-chloroethyl) formal, 10.8 g of 1,2,3-trichloropropane, 12.2 g of a 50 wt % aqueous solution of tetrabutylammonium bromide, 524.5 g of a 42% aqueous solution of sodium hydrosulfide, 725 g of water, 11.0 g of sulfur and 286.7 g of a 48% aqueous solution of sodium hydroxide were reacted, whereby a pale yellow clear liquid polymer was obtained without going through a solid polysulfide. The average value of repeating numbers r of sulfur, SH content, viscosity, specific gravity, glass transition temperature and temperature of 50% weight loss of the obtained polymer are shown in Table 1.

Example 8

Using a 2-L separable flask, 640.0 g of bis(2-chloroethyl) formal, 12.1 g of a 50 wt % aqueous solution of tetrabutylammonium bromide, 514.2 g of a 42% aqueous solution of sodium hydrosulfide, 565 g of water, 11.1 g of sulfur and 288.3 g of a 48% aqueous solution of sodium hydroxide were reacted, whereby a pale yellow clear liquid polymer was obtained without going through a solid polysulfide. The average value of repeating numbers r of sulfur, SH content, viscosity, specific gravity, glass transition temperature and temperature of 50% weight loss of the obtained polymer are shown in Table 1.

Example 9

Using a 2-L separable flask, 640.0 g of bis(2-chloroethyl) formal, 12.1 g of a 50 wt % aqueous solution of tetrabutylammonium bromide, 589.4 g of a 42% aqueous solution of sodium hydrosulfide, 482 g of water, 9.5 g of sulfur and 246.5 g of a 48% aqueous solution of sodium hydroxide were reacted, whereby a pale yellow clear liquid polymer was obtained without going through a solid polysulfide. The average value of repeating numbers r of sulfur, SH content, viscosity, specific gravity, glass transition temperature and temperature of 50% weight loss of the obtained polymer are shown in Table 1.

TABLE 1

| No. | Polymer | Average value of sulfur repeating numbers r | SH content (%) | Viscosity (Pa · s) | Glass transition temperature (° C.) | Specific gravity (@ 23° C.) | Temperature of 50% weight loss (° C.) |
|---|---|---|---|---|---|---|---|
| 1 | Polymer of Comparative Example 1 Blend of Thiokol "LP-3" and "LP-23" (ratio 6:4) (Manufactured by Toray Fine Chemical Co., Ltd.) | 2.0 | 5.2 | 3.0 | −64 | 1.27 | 306 |
| 2 | Polymer of Example 1 | 1.8 | 5.2 | 2.0 | −66 | 1.25 | 311 |
| 3 | Polymer of Example 2 | 1.5 | 5.1 | 1.4 | −69 | 1.23 | 317 |

TABLE 1-continued

| No. | Polymer | Average value of sulfur repeating numbers r | SH content (%) | Viscosity (Pa · s) | Glass transition temperature (° C.) | Specific gravity (@ 23° C.) | Temperature of 50% weight loss (° C.) |
|---|---|---|---|---|---|---|---|
| 4 | Polymer of Example 3 | 1.1 | 5.1 | 1.1 | −73 | 1.21 | 332 |
| 5 | Polymer of Comparative Example 2 | 1.0 | 5.1 | 1.0 | −77 | 1.20 | 338 |
| 6 | Polymer of Comparative Example 3 Blend of Thiokol "LP-3" and "LP-2" (ratio 1:9) (Manufactured by Toray Fine Chemical Co., Ltd.) | 2.0 | 2.3 | 35.0 | −57 | 1.29 | 305 |
| 7 | Polymer of Example 4 | 1.8 | 2.2 | 25.2 | −60 | 1.27 | 310 |
| 8 | Polymer of Example 5 | 1.5 | 2.3 | 17.5 | −64 | 1.26 | 315 |
| 9 | Polymer of Example 6 | 1.3 | 2.2 | 14.9 | −67 | 1.25 | 324 |
| 10 | Polymer of Example 7 | 1.1 | 2.3 | 10.5 | −70 | 1.22 | 334 |
| 11 | Polymer of Example 8 | 1.1 | 1.8 | 9.1 | −74 | 1.21 | 340 |
| 12 | Polymer of Example 9 | 1.1 | 7.6 | 0.3 | −81 | 1.20 | 317 |

The characteristic values of the polymers used for the evaluation are shown in Table 1. The polymers of Nos. 2 to 4 and 7 to 12 are our polymers. When the polymers of Nos. 1 to 5, which had approximately the same SH contents, were compared, the polymers of Examples 1 to 3 and Comparative Example 2, which had the average values of the repeating numbers of sulfur r of 1.8 or less, had lower viscosities, lower glass transition temperatures and lower specific gravities, more increased temperatures of 50% weight loss and better heat resistances than those of the polymer of Comparative Example 1, which had an average value of r of 2.0. Furthermore, when the polymers of Nos. 6 to 10, which had approximately the same SH contents, were compared, the polymers of Examples 5 to 8, which had the average values of the repeating numbers of sulfur r of 1.1 or more and 1.8 or less, had lower viscosities, lower glass transition temperatures and lower specific gravities, more increased temperatures at 50% weight loss and better heat resistances than those of the polymer of Comparative Example 3, which had an average value of r of 2.0.

When the polymers having approximately the same SH contents were compared, the polymers having lower average values of r had lower viscosities, and thus when the polymers are to be incorporated as sealants, it is possible to decrease the additional amount of a solvent for ensuring workability.

Examples 10 to 12

18 parts by weight of manganese dioxide (TYPE-FA manufactured by Honeywell), and 35 parts by weight of SRF carbon, 18 parts by weight of butyl benzyl phthalate and 0.9 parts by weight of tetrabutylthiuram disulfide (Ouchi Shinko Chemical Industrial Co., Ltd., Nocceller TBT) as additives were added to 100 parts by weight of each of the polymers of Examples 1 to 3 (Nos. 2 to 4), and the mixture was kneaded by using a triple roll mill. 38 g of the mixture in total was put between iron plates that had been adjusted to give a gap of 2 mm and cured by heating at 70° C. for 2 hours to prepare a sheet-like cured composition having a thickness of 2 mm. The obtained sheet was left under an atmosphere at 23° C., 50% RH for 1 hour to remove the heat. The specific gravity, glass transition temperature, temperature of 50% weight loss, elastic recovery, hardness and dumbbell physical characteristic value were measured with the cured product that had been cut out into about 20 mm square. The specific gravity is shown in Table 2, and the other physical properties are shown in Table 3.

Comparative Example 4

A curable composition was prepared in a similar manner to that in Examples 10 to 12 by using No. 1 (a polymer obtained by blending Thiokol "LP-3" and "LP-23" manufactured by Toray Fine Chemicals Co., Ltd. at a ratio of 6:4) as a polymer, and the specific gravity was measured, and the result of the measurement is shown in Table 2. Furthermore, the glass transition temperature, temperature of 50% weight loss, elastic recovery, hardness and dumbbell physical characteristic values of a sheet-like cured product having a thickness of 2 mm were obtained. The obtained results are shown in Table 3.

Examples 13 to 16

9 parts by weight of manganese dioxide (TYPE-FA manufactured by Honeywell), and 35 parts by weight of SRF carbon, 9 parts by weight of butyl benzyl phthalate and 0.45 parts by weight of tetrabutylthiuram disulfide (Ouchi Shinko Chemical Industrial Co., Ltd., Nocceller TBT) as additives were added to 100 parts by weight of each of the polymers of Examples 4 to 7 (Nos. 7 to 10), and the mixture was kneaded by using a triple roll mill. 34 g of the mixture in total was put between iron plates that had been adjusted to give a gap of 2 mm and cured by heating at 70° C. for 2 hours to prepare a sheet-like cured composition having a thickness of 2 mm. The obtained sheet was left under an atmosphere at 23° C., 50% RH for 1 hour to remove the heat. The specific gravity of the cured product that had been cut out into about 20 mm square was measured. The result is shown in Table 2.

Comparative Example 5

A curable composition was prepared in a similar manner to that in Examples 13 to 16 by using No. 6 (a polymer obtained by blending Thiokol "LP-3" and "LP-2" manufactured by Toray Fine Chemicals Co., Ltd. at a ratio of 1:9) as a polymer, and the specific gravity was measured, the result of the measurement is shown in Table 2.

TABLE 2

| | Example 10 | Example 11 | Example 12 | Comparative Example 4 | Example 13 | Example 14 | Example 15 | Example 16 | Comparative Example 5 |
|---|---|---|---|---|---|---|---|---|---|
| No. | 2 | 3 | 4 | 1 | 7 | 8 | 9 | 10 | 6 |
| Average value of sulfur repeating numbers r | 1.8 | 1.5 | 1.1 | 2.0 | 1.8 | 1.5 | 1.3 | 1.1 | 2.0 |
| Specific gravity | 1.40 | 1.39 | 1.37 | 1.41 | 1.41 | 1.41 | 1.40 | 1.38 | 1.43 |

From Table 2, the curable compositions Examples 10 to 16, which used the polysulfide polymers (Nos. 2 to 4 and 7 to 10) having the average values of repeating numbers of sulfur r in the range of from 1.1 to 1.8, had lower specific gravities than those of the cured products of Comparative Examples 4 and 5, which used the polysulfide polymers (Nos. 1 and 6), which are generally used and have an average value of r of 2.0. The curable compositions using the polysulfide polymers each having an average value of r in the range of from 1.1 to 1.8 are suitable for purposes of use for which further weight saving is required.

Comparative Example 6

A sheet-like curable composition having a thickness of 2 mm was prepared by using No. 5 (the polymer of Comparative Example 2) as a polymer in a similar manner to that in Examples 10 to 12, and the glass transition temperature, temperature of 50% weight loss, elastic recovery, hardness and dumbbell physical characteristic values were obtained. The obtained results are shown in Table 3.

TABLE 3

| | Example 10 | Example 11 | Example 12 | Comparative Example 4 | Comparative Example 6 |
|---|---|---|---|---|---|
| No. | 2 | 3 | 4 | 1 | 5 |
| Average value of sulfur repeating numbers r | 1.8 | 1.5 | 1.1 | 2.0 | 1.0 |
| Glass transition temperature (° C.) | −57 | −60 | −66 | −57 | −68 |
| Temperature of 50% weight loss (° C.) | 313 | 326 | 337 | 306 | 339 |
| Hardness (ShoreA) | 45 | 43 | 35 | 46 | 4 |
| M100 (N/mm2) | 1.01 | 0.95 | 0.69 | 1.06 | 0.08 |
| Tmax (N/mm2) | 2.67 | 2.32 | 2.03 | 2.84 | 0.57 |
| Emax (%) | 260 | 263 | 325 | 301 | 898 |
| Elastic recovery (%) | 60 | 65 | 75 | 58 | 73 |

From Table 3, the curable compositions of Examples 10 to 12, which used the polysulfide polymers (Nos. 2 to 4) each having an average value of repeating numbers of sulfur r in the range of from 1.1 to 1.8, combined a lower glass transition temperature, a higher heat resistance and a higher elastic recovery than those of the cured product of Comparative Example 4 using a general used polysulfide polymer (No. 1) having an average value of r of 2.0. The curable composition of Comparative Example 6, which had an average value of repeating numbers of sulfur r of 1.0, had a low glass transition temperature and high heat resistance, but had a very low hardness as 4, and also had low M100 and Tmax in the dumbbell tensile test, and thus the cured product was not suitable for practical use.

From the results in Tables 2 and 3, the curable compositions using the thiol group-containing polymers having an average value of r from 1.1 to 1.8 are suitable for sealants for aircraft for which further weight saving and adaptation in broader temperature ranges are required.

Example 17

A base component was prepared by adding the compounding agents shown in Table 4 to 100 parts by weight of the polymer of Example 3 (No. 4, the average value of r was 1.1) and by using a planetary mixer, and 134 parts by weight of hexamethylene diisocyanate (Duranate 50M-HDI manufactured by Asahi Kasei Corporation, NCO content 5.0%) was further added thereto, and the mixture was thoroughly kneaded by manual kneading. The mixture was formed into a sheet-like shape of 50 mm×12 mm×3 mm thickness on an aluminum plate and cured at 23° C. for 3 days then at 50° C. for 3 days, whereby a cured product was obtained. The obtained cured product was subjected to evaluation of accelerated weather resistance by using S. W. O. M. The obtained result is shown in Table 4.

Comparative Example 7

A cured product having a thickness of 3 mm using the polymer of Comparative Example 2 (No. 5, the average value of r was 1.0) was prepared in a similar manner to Example 17, and the accelerated weather resistance was evaluated by using S. W. O. M. The obtained result is shown in Table 4.

TABLE 4

| | | Example 17 | Comparative Example 7 |
|---|---|---|---|
| Polymer No. | | 4 | 5 |
| Average value of sulfur repeating numbers r | | 1.1 | 1.0 |
| Formulation | | Parts by weight | |
| Base component | Polymer | 100 | 100 |
| | Trioctylamine (Farmin T-08 manufactured by Kao Corporation) | 0.3 | 0.3 |
| | Antioxidant (Adekastab AO-80 manufactured by ADEKA Corporation) | 1 | 1 |
| | Antioxidant (Adekastab AO-412S manufactured by ADEKA Corporation) | 1 | 1 |
| | Plasticizer (Benzoflex 9-88 manufactured by CBC) | 70 | 70 |

TABLE 4-continued

| | | | |
|---|---|---|---|
| | Calcium carbonate (Hakuenka CCR manufactured by Shiraishi Calcium Kaisha Ltd.) | 100 | 100 |
| HDI monomer | HDI (Duranate M50-HDI manufactured by Asahi Kasei Corporation) | 134 | 134 |

| Result of evaluation of accelerated weather resistance | State | |
|---|---|---|
| S.W.O.M. 500 h | ○ | ○ |
| S.W.O.M. 1,000 h | ○ | x |
| S.W.O.M. 1,500 h | ○ | x |
| S.W.O.M. 2,000 h | ○ | x |

We confirmed from Table 4 that generation of cracks was prevented from occurring and weather resistance was improved in Example 17 having an average value of repeating numbers of sulfur r of 1.1 (Sample 4) as compared to Comparative Example 7 having an average value of r of 1.0 (No. 5).

It is understood from the results of the dumbbell tensile physical properties in Table 3 and the weather resistance in Table 4 that the curable composition using the polysulfide polymer having an average value of r of 1.1 was different in properties from when the polymer having an average value of r of 1.0 was used.

Example 18

100 parts by weight of "Epicoat 828," which is an epoxy resin manufactured by Japan Epoxy Resin, and 5 parts by weight of "ADEKA Hardener EHC30," which is an aromatic tertiary amine manufactured by ADEKA Corporation, were thoroughly kneaded by manual kneading with respect to 100 parts by weight of the polymer of Example 3 (No. 4, the average value of r was 1.1), and the mixture was cured at 23° C. for 7 days, whereby a test piece having a thickness of 1 cm was prepared. The glass transition temperature and temperature of 50% weight loss of the obtained curable composition were measured. The obtained results are shown in Table 5.

Comparative Example 8

A curable composition was prepared in a similar manner to Example 18 by using Sample 1 (a polymer obtained by blending Thiokol "LP-3" and "LP-23" manufactured by Toray Fine Chemical Co., Ltd. at a ratio of 6:4) instead of the polymer of Example 3, and the glass transition temperature and temperature of 50% weight loss were measured. The obtained results are shown in Table 5.

TABLE 5

| | Example 18 | Comparative Example 8 |
|---|---|---|
| No. | 4 | 1 |
| Average value of sulfur repeating numbers r | 1.1 | 2.0 |

TABLE 5-continued

| | Example 18 | Comparative Example 8 |
|---|---|---|
| Temperature of 50% weight loss (° C.) | 369 | 353 |
| Glass transition temperature (° C.) | 42 | 47 |

As shown in Table 5, we confirmed that the curable composition of Example 18, which used the thiol group-containing polymer having an average value of repeating number of sulfur r of 1.1 (No. 4), showed a lower glass transition temperature and higher heat resistance than those of the cured product of Comparative Example 8, which used a generally used polysulfide polymer having an average value of r of 2.0 (No. 1).

INDUSTRIAL APPLICABILITY

The thiol group-containing polymer has a lower specific gravity, a lower viscosity, a lower glass transition temperature and higher heat resistance than those of conventional polysulfide polymers, by decreasing the repeating number of sulfur in the polysulfide bonds and, thus, can be used in sealants, adhesives, paints and the like for which properties of a low specific gravity, a low viscosity and a low glass transition temperature are required. Furthermore, since our curable composition has improved elastic recovery and improved weather resistance, it can be used in sealants, adhesives, paints and the like for which elastic recovery and weather resistance are required.

The invention claimed is:

1. A method of producing a thiol group-containing polymer comprising:
    reacting bis(2-chloroethyl) formal with sodium hydrosulfide in the presence of a phase transfer catalyst,
    wherein the thiol group-containing polymer is represented by general formula:

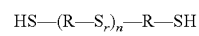
    HS—(R—S$_r$)$_n$—R—SH where R is an organic group including a —C$_2$H$_4$—O—CH$_2$—O—C$_2$H$_4$— structure, n is an integer of from 1 to 200, r is an integer of from 1 to 5, and the average value of r is 1.1 or more and lower than 1.8, and
    the thiol group-containing polymer is a liquid polymer.

2. The method according to claim 1, wherein R is an organic group including 50 mol % or more of —C$_2$H$_4$—O—CH$_2$—O—C$_2$H$_4$— structure.

3. A method of producing a thiol group-containing polymer comprising:
    reacting bis(2-chloroethyl) formal and 1,2,3-trichloropropane with sodium hydrosulfide in the presence of a phase transfer catalyst,
    wherein the thiol group-containing polymer is represented by general formula:

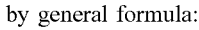
    HS—(R—S$_r$)$_n$—R—SH where R is an organic group including a —C$_2$H$_4$—O—CH$_2$—O—C$_2$H$_4$— structure and formula (1):

structure, n is an integer of from 1 to 200, r is an integer of from 1 to 5, and the average value of r is 1.1 or more and lower than 1.8, and the thiol group-containing polymer is a liquid polymer.

4. The method according to claim 3, wherein R is an organic group including 50 mol % or more of $-C_2H_4-O-CH_2-O-C_2H_4-$ structure.

* * * * *